(12) United States Patent
Suekane et al.

(10) Patent No.: US 6,365,795 B1
(45) Date of Patent: Apr. 2, 2002

(54) ABSORPTIVE ARTICLE CONTAINING TITANIUM OXIDE

(75) Inventors: Makoto Suekane; Satoshi Mizutani; Katsushi Tomita; Etsuko Tagami, all of Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/644,888

(22) Filed: Aug. 23, 2000

(30) Foreign Application Priority Data

Aug. 27, 1999 (JP) .......................................... 11-241055

(51) Int. Cl.[7] .................................................. A61F 13/15
(52) U.S. Cl. ......................... 604/370; 604/367; 604/372
(58) Field of Search ................................. 604/367, 370, 604/372

(56) References Cited

U.S. PATENT DOCUMENTS 6,302,872 B1 * 10/2001 Teranishi et al. ...... 604/385.23

FOREIGN PATENT DOCUMENTS

| JP | 3-30764 | 2/1991 |
|---|---|---|
| JP | 5-25764 | 2/1993 |
| JP | 5-176953 | 7/1993 |

\* cited by examiner

*Primary Examiner*—John G. Weiss
*Assistant Examiner*—Michael Bogart
(74) *Attorney, Agent, or Firm*—Darby & Darby

(57) ABSTRACT

There is disclosed an absorptive article including a liquid-permeable surface material on a liquid receiving side. The surface material is formed of a nonwoven fabric including an upper layer to face the skin of a wearer, and a lower layer positioned under the upper layer. At least the fibers forming the upper layer contain titanium oxide. The fibers forming the lower layer have a lower elongation percentage and a higher tensile strength, as measured according to the JIS L 1013, than those of the fibers forming the upper layer.

7 Claims, 1 Drawing Sheet

ABSORPTIVE ARTICLE CONTAINING TITANIUM OXIDE

BACKGROUND OF THE INVENTION

1. Field of the Invention

The present invention relates to an absorptive article such as a hygienic napkin, panty liners, a disposable diaper or a urine pad. More specifically, the invention relates to an absorptive article which uses a surface material which is bulky and smooth on its surface and has a high performance to hide the discharges absorbed in an absorbent.

2. Related Art

In the prior art, there have been widely used absorptive articles for absorbing the discharges, such as hygienic napkins, panty liners, disposable diapers or urine pads. Each of these absorptive articles is constructed to include: a liquid-permeable surface sheet to come into contact with the skin of a wearer; a liquid-impermeable back sheet; and an absorbent layer sandwiched between the surface sheet and the back sheet. Since this surface sheet is made liquid-permeable, it allows the color of the discharges (e.g., menstrual blood), as passed through the surface sheet and absorbed by the absorbent layer, to be seen through the surface sheet. This may cause the user to feel uncomfortable.

In this respect, it has been investigated to make the once absorbed discharges unseen through the surface sheet. In Unexamined Published Japanese Patent Application No. H3-30764, for example, there is disclosed a facing non-woven fabric for a sanitary material which is formed of thermoplastic fibers containing titanium dioxide. By incorporating the titanium oxide into the fibers, the whiteness of the nonwoven fabric is enhanced to enhance the hiding properties. This nonwoven fabric has a single-layered structure. In Unexamined Published Japanese Patent Application No. H5-25764, on the other hand, there is disclosed an absorptive article containing a surface material having a two-layered structure. In the individual layers of the surface material, there is contained the titanium oxide to further enhance the hiding properties.

However, the fibers containing the titanium oxide are cut out with a high draft so that they are spun at a low draft. As a result, the fibers containing the titanium oxide generally have a low resin orientation so that their dry elongation percentage is raised while lowering the tensile strength. Therefore, the fibrous web, as formed of the fibers containing the titanium oxide, is lowered in its strength and is also hard to make bulky. Since the bulkiness drops, moreover, the so-called "re-wetting" (i.e., the phenomenon in which the once absorbed body liquids will ooze again to the surface) easily occurs.

Therefore, the above-specified problems are left unsolved even if the nonwoven fabric having the single-layered structure, as disclosed in Unexamined Published Japanese Patent Application No. H3-30764, and the nonwoven fabric having the two-layered structure containing the titanium oxide in each layer, as disclosed in Unexamined Published Japanese Patent Application No. H5-25764, are used as the surface material of the absorptive article such as the hygienic napkin.

SUMMARY OF THE INVENTION

An object of the invention is to provide an absorptive article which uses a bulky surface material having high levels of hiding properties.

According to the invention, there is provided an absorptive article comprising a liquid-permeable surface material on a liquid receiving side, wherein the surface material is formed of a nonwoven fabric including an upper layer to face the skin of a wearer, and a lower layer positioned under the upper layer, wherein at least the fibers forming the upper layer contain titanium oxide, and wherein the fibers forming the lower layer have a lower elongation percentage and a higher tensile strength, as measured according to the JIS L 1013, than those of the fibers forming the upper layer.

The surface material of the invention contains the titanium oxide in its upper layer so that it can have such a high whiteness as to hide the passed discharges effectively. On the other hand, the lower layer is formed of fibers having a relatively low elongation percentage and a high tensile strength so that it can provide the bulkiness and the cushioning properties. As a result, the presence of the upper layer hardly gives a visual uncomfortableness to the wearer, and the presence of the lower layer can improve the wearing feel. Moreover, the presence of the lower layer can easily prevent the re-wetting thereby to improve the wearing feel better. Here, the surface material is soft as a whole.

The fibers forming the lower layer preferably contain no titanium oxide, or the fibers forming the lower layer preferably have a smaller content (in wt. %) of titanium oxide than that (in wt. %) of titanium oxide of the fibers forming the upper layer.

On the other hand, the fibers forming the lower layer preferably have an elongation percentage of 50 to 80%, as measured according to the JIS L 1013, and a tensile strength of 2 to 5 gram/denier (g/d), as measured according to the JIS L 1013.

The fibers forming the upper layer preferably contain 0.5 to 10 wt. % of titanium oxide.

The fibers forming the lower layer preferably contain 0 to 1 wt. % of titanium oxide.

It is preferred that the fibers forming the upper layer are thermoplastic and have a core-sheath structure, the cores of which contain the titanium oxide. In this case, the surface material including the upper layer and the lower layer is preferably an air-through bonded nonwoven fabric.

The lower layer preferably has a basis weight of 7 to 45 g/m².

The upper layer preferably has a basis weight of 5 to 20 g/m².

The fineness of the fibers forming the upper layer is preferably higher than that of the fibers forming the lower layer. In this case, the fineness of the fibers forming the lower layer is preferably 1 to 5 deniers. On the other hand, the fineness of the fibers forming the upper layer is preferably 2 to 6 deniers.

DESCRIPTION OF THE PREFERRED EMBODIMENT

Figure 1:
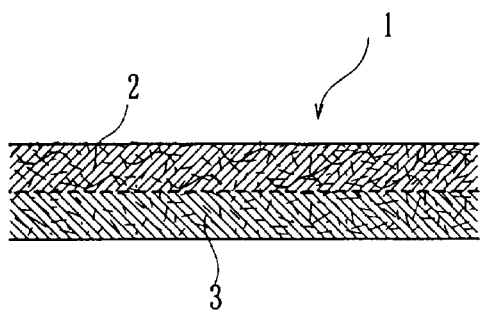
FIG. 1 is a sectional view showing a surface material.
Figure 2:
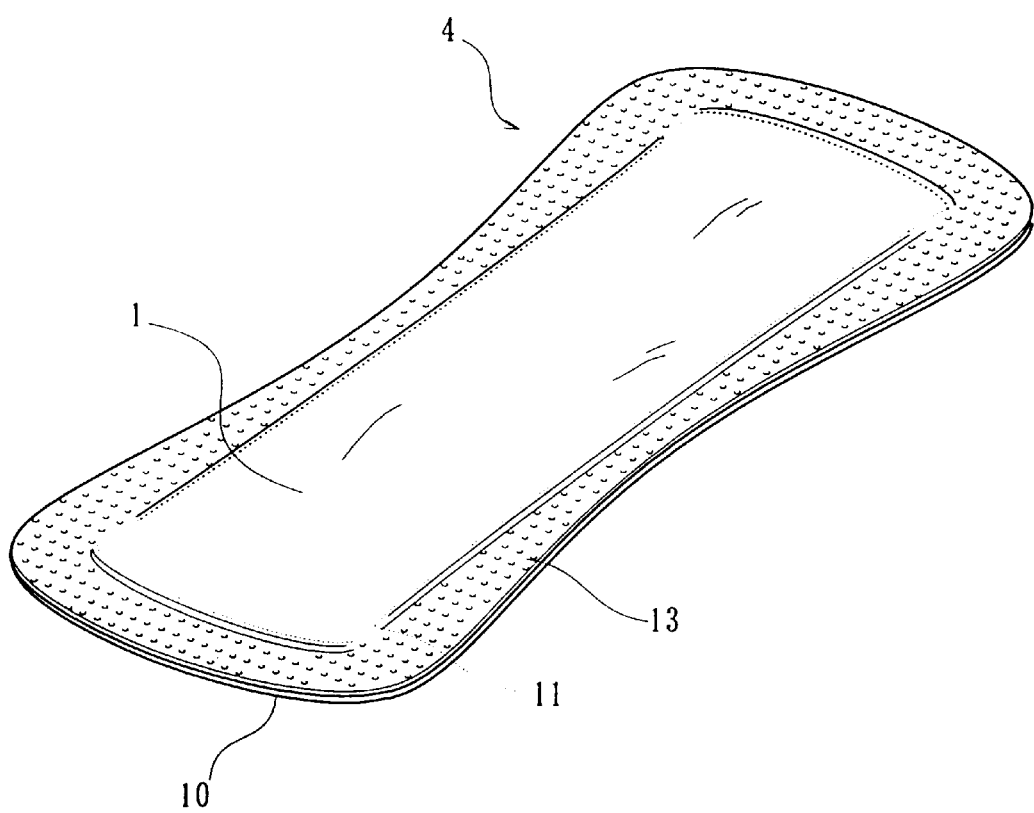
FIG. 2 is a perspective view of an absorptive article using the surface material in accordance with one embodiment of the invention.

The invention will be described with reference to the accompanying drawing, in which: FIG. 1 is a sectional view showing a surface material; and FIG. 2 is a perspective view of an absorptive article using the surface material in accordance with one embodiment of the invention.

A surface material 1 to be used in the absorptive article of the invention is constructed to include an upper layer 2 to be applied to the skin of a wearer, and a lower layer 3 lying under the upper layer, as shown in FIG. 1. In other words, the surface material 1 is made of an integral nonwoven fabric in which the upper layer 2 and the lower layer 3 are formed of different fibrous layers. This surface material 1 is used to construct the absorptive article such as a hygienic napkin 4, as shown in FIG. 2.

The fibers forming the upper layer 2 of the surface material 1 contain titanium oxide (e.g., titanium dioxide: $TiO_2$) in 0.5 to 10 wt. %. If the content is lower than the lower limit, the whiteness or brightness will fail to rise to a sufficient height. As a result hiding properties necessary for the body liquids absorbed cannot be obtained. If the content is higher than the upper limit, the fibers are difficult to spin at the manufacture. The fibers forming the upper layer 2 contain the titanium oxide so that they have a large elongation percentage when dried. As a result, the surface material 1 has a high surface smoothness and is soft.

(JIS L 1013)

In the accordance with JISL 1013, after a specimen is attached to grippers of a tensile tester in a lightly tensed state, a test is conducted under the condition where a gripping interval is 20 mm and a pulling speed is 20 mm/min. Extension when an initial load is applied is read to be a relaxed length (mm). Then the specimen is pulled, and load (N) {gf} and extension (mm) are measured at the time when the specimen is broken. Tensile strength (N/tex) {gf/D} and elongation (%) are calculated as following. Tests are conducted ten times to obtain average values. Tensile strength is calculated to two decimal places and the elongation percentage is calculated to one decimal place, respectively.

$$\text{Tensile strength } (N/tex)\{gf/D\}=SD/d$$

wherein

SD: Strength at break (N) {gf} d: Fineness based on corrected mass of specimen (tex) {D}

$$\text{Elongation percentage } (\%)=(E_2-E_1)/(L+E_1)\times 100$$

wherein $E_1$: Relaxed length (mm)

$E_2$: Elongation at break (mm) or Elongation at maximum load (mm)

L: Gripping Interval (mm)

(JIS L 1096)

In this case, three pieces of specimen having a width of 25 mm are prepared. The specimen is gripped by grippers of a fabric tensile tester under an initial load corresponding to a load to 10 m of specimen. The test is conducted under the condition that a chuck distance is 100 mm and a pulling speed is 100 mm/min to measure a strength (N) {kgf} and elongation percentage (%) at break. The tests are conducted three times in both MD and CD respectively, to obtain average values (in three effective figures).

(JIS L 1018)

(Method A: 45-Degree Cantilever Method)

Here, five pieces of specimen of 2 cm×about 15 cm are cut out in MD and CD, respectively. The specimen is placed on a horizontal table having a smooth surface and a 45-degree slope at one end thereof while aligning the shorter side of the specimen on a basic line of a scale. Then, the specimen is slowly slid toward the slope by an appropriate manner. When one end of the specimen comes into contact at the center thereof with the slope the position of the other end of the specimen is read by the scale. Bending resistance is expressed by the migration length (mm) of the specimen. The respective five pieces of specimen are tested at both surface side and back side to obtain average values in MD and CD, respectively (to integral number).

In order that the lower layer 3 may be more bulky and may have greater cushioning properties that the upper layer 2, on the other hand, the fibers forming the lower layer 3 preferably have a lower elongation percentage in a dry state according to the JIS (Japanese Industrial Standards) L 1013 and a higher tensile strength according to JIS L 1013 than the fibers forming the upper layer 2. The elongation percentage is preferably 50 to 80%. If the elongation percentage is lower than the lower limit, the fibers are hard and are less desirable to touch. If the upper limit is exceeded, sufficient bulkiness and strength are hard to obtain. Moreover, the tensile strength is preferably 2 to 5 g/d. Under the lower limit, the fibers have an inferior bulkiness. Over the upper limit, the fibers are hard such that they become less desirable to touch. In the presence of the bully lower layer 3, it is possible to prevent the re-wetting.

The fibers forming the lower layer 3 can be those containing no foreign substance such as the titanium oxide so that they may have such an elongation percentage and strength. When the fibers containing a foreign substance such as the titanium oxide are to be spun, they are ordinarily spun with a lowered draft because they are cut with a high draft. As a result, the fibers are made to have a low resin orientation, a relatively high elongation percentage and a low tensile strength. On the other hand, the fibers containing no or little foreign substance such as the titanium oxide are not cut even if the draft is raised at the spinning step. This makes it possible to spin the fibers of a high resin or orientation by raising the draft thereby to produce fibers of a low elongation percentage and a high tensile strength.

In order to enhance the hiding properties of the surface material 1, however, the titanium oxide can also be contained a little or preferably 0.1 to 1 wt. % in the fibers to form the lower layer 3. If this upper limit is exceeded, the draft at the fiber spinning time has to be lowered thereby to raise the elongation percentage of and lower the tensile strength of the fibers so that the bulkiness and the cushioning properties necessary for the lower layer 3 are hard to obtain.

Here the fibers forming the upper layer 2 in a dry state preferably have an elongation percentage of 60 to 90% according to the JIS L 1013. Under this lower limit, the fibers are so hard such that they become less desirable to touch. Over the upper limit, the fibers are hard to card at the manufacture. Here, the measuring conditions of the elongation percentage in the dry state are a gripping interval of 20 mm and a pulling speed of 20 mm/min. On the other hand, the fibers forming the upper layer 2 in the dry state preferably have a tensile strength of 1 to 4 g/d according to the JIS L 1013. Under this lower limit, the fibers are difficult to card at the manufacture. Over the upper limit, the fibers become so hard such that they are less desirable to touch.

The fibers of the upper layer 2 and the lower layer 3 preferably have the core-sheath structure made of a thermoplastic resin. In this case, the surface material 1 formed of the upper layer 2 and the lower layer 3 can be made of a heat-treated nonwoven fabric such as an air-through bonded nonwoven fabric. In this manufacturing method, the individual fibers of the upper layer 2 and the lower layer 3 are fed from a carding machine to form a fibrous web of a two-layered structure and are individually heat-treated by an air-through bonding dryer to bond them.

The fibers made of the thermoplastic resin and having the core-sheath structure are exemplified by fibers having cores filled with polypropylene or polyethylene terephthalate and sheaths of polyethylene. These fibers are used to form the nonwoven fabric in the air-though bonding dryer by preferably treating them at 135 to 140° C. in the dryer and at 120 to 130° C. in a heat cylinder.

When the upper layer 2 is to be formed of the fibers having such core-sheath structure, it is preferred that the titanium oxide is mainly contained in the resin forming cores. When the nonwoven fabric is to be manufactured by using such fibers, the sheaths are fused to joint each other, but the titanium oxide in the core can be prevented from flowing out at the fusing time. Since the joints between the fibers are not blocked by the presence of the titanium oxide, on the other hand, there is such a merit in the manufacturing process that a high temperature is not established for the joints. Moreover, the jointing treatment does not deteriorate the texture of the nonwoven fabric obtained. Still moreover, the titanium oxide in the cores will cause less polarization in the whiteness. Thus, the fibers forming the upper layer 2 are preferably made to contain 0.5 to 10 wt % of titanium oxide (with respect to the total fiber weight) in the cores but not in the sheaths.

When the fibers forming the lower layer 3 are also fibers having the core-sheath structure and when the titanium oxide is contained in the fibers forming the lower layer 3, the titanium oxide is preferably contained in 0 to 1% (with respect to the total fiber weight) in the resin forming the filled cores but not in the sheaths.

In order to cause the cushioning properties to appear in the lower layer 3, this lower layer 3 preferably has a basis weight (this may be referred to as "METSUKE") of 7 to 45 $g/m^2$. Under this lower limit, the suction of the body liquids may become difficult. Over the upper limit, the liquids are easily held, while passing, by the lower layer 3 to lower their transfer to an absorbent member positioned beneath it. On the other hand, the upper layer 2 preferably has a basis weight of 5 to 20 $g/m^2$. Under this lower limit, the surface may find it difficult to keep a necessary softness. Over the upper limit, the upper layer 2 may be so hard to permeate the liquids as to get clogged.

For the cushioning properties, on the other hand, the fibers of the lower layer 3 preferably have a fineness of 1 to 5 d. Under this lower limit, the liquids are so easily held, while passing, by the lower layer 3 as to lower the transfer to the absorbent member. Over the upper limit, the transfer of the liquids from the upper layer 2 to the lower layer 3 may be difficult. On the other hand, the fibers of the upper layer 2 preferably have a fineness of 2 to 6 d. Under this lower limit, the discharge liquids may not pass, but the water content may remain on the surface. Over the upper limit, the surface material 1 may have a lowered feeling.

Here, the fibers forming the upper layer 2 preferably have a denier equal to or higher than that of the fibers forming the lower layer 3. With these deniers, the discharge liquids will easily transfer from the upper layer 2 to the lower layer 3.

The hygienic napkin 4, as shown in FIG. 2, is constructed to include: the surface material 1 having the aforementioned two-layered structure; a liquid impermeable back sheet 10; and an absorbent member 11 sandwiched between the surface material 1 and the back sheet 10. In a peripheral portion 13 of the hygienic napkin 4 and in the region where the absorbent member 11 is absent, the surface material 1 and the back sheet 10 are jointed by a heat embossing method, an adhesive, or the like. When the hygienic napkin 4 is used, the menstrual blood passes sequentially through the upper layer 2 and the lower layer 3 of the surface material 1 until it is absorbed by the underlying absorbent member 11.

Here, the surface material of the invention can be applied not only to the hygienic napkin thus far described but also to absorptive articles such as pantie liners, disposable diapers or urine pads.

EXAMPLES

The examples of the invention will be described, but the invention should not be limited to them.

As the surface material 1, the nonwoven fabric having the upper layer 2 and the lower layer 3 of the following constructions was manufactured by the following methods.

Fibers and Web Constructing the Upper Layer

There were used the thermally fusible fibers of a fineness of 3d and a fiber length of 51 mm, including: cores (filled with a resin) of PET (polyethylene terephthalate); and sheaths of PE (polyethylene). In the resin forming the cores, there was contained titanium oxide ($TiO_2$) in 2 wt. % with respect to the total fiber weight (i.e., the summed weight of the cores and the sheaths). The thermally fusible fibers used had an elongation percentage of 70% and a tensile strength of 3 g/d in the dry state. These fibers were used to form the fibrous web for the upper layer having a basis weight of 10 $g/m^2$.

Fibers and Web Constructing the Lower Layer

There were used the thermally fusible fibers of a fineness of 3 d and a fiber length of 51 mm, including: cores (filled with a resin) of PET; and sheaths of PE. In the resin forming the cores, there was contained titanium oxide ($TiO_2$) in 0.1 wt. % with respect to the total fiber weight (i.e., the summed weight of the cores and the sheaths). The thermally fusible fibers had an elongation percentage of 60% and a tensile strength of 3.5 g/d in the dry state. These fibers were used to form the fibrous web for the upper layer having a basis weight of 15 $g/m^2$.

Process for Manufacturing Nonwoven Fabric for Surface Material

The air-through bonded nonwoven fabric for the surface material was obtained by feeding the fibers from the carding machine to form a two-layered web, in which the fibrous web of the upper layer was laid over the fibrous web of the lower layer, and by treating the two-layered web at 135 to 140° C. in the dryer and at 120 to 130° C. in the heat cylinder of the air-through bonding dryer.

The surface material (or the nonwoven fabric) obtained had a total basis weight of 25 $g/m^2$ and a total thickness of 0.7 mm. The tensile strengths of the surface material were measured in both the MD (Machine Direction) and the CD (Cross Direction) according to JIS L 1096 with a chuck distance of 100 mm; a material width of 25 mm; and a pulling speed of 100 mm/min. In the MD, the tensile strengths were 300 g/inch (at an elongation of 5%) and 1,800 g/inch (at the maximum). In the CD, the tensile strengths were 15 g/inch (at an elongation of 5%) and 270 g/inch (at the maximum). On the other hand, the bending resistance, as measured by the cantilever method according to the JIS L 1018, was 90 mm in the MD and 45 mm in the CD. This surface material had a high bulkiness and high hiding properties. Moreover, the surface material was excellent not only in the liquid permeability but also in the re-wet prevention.

As has been described in detail hereinbefore, the surface material of the invention contains the titanium oxide in its upper layer so that its whiteness can be great enough to hide the passed discharges effectively. On the other hand, the lower layer is formed of the fibers having a relatively low elongation percentage so that it can give the bulkiness and the cushioning properties. As a result, the presence of the upper layer gives little visual uncomfortableness to the wearer, and the presence of the lower layer improves the wearing feel. Moreover, the surface material is soft as a whole. Here, the presence of the lower layer can easily prevent the re-wetting to further improve the wearing feel.

By adjusting the deniers of the fibers forming the individual layers, moreover, the surface material can be made to have high levels of liquid transferring properties.

Here, "comprises/comprising" when used in this specification is taken to specify the presence of stated features, integers, steps or components but does not preclude the presence or addition of one or more other features, integers, steps, components or groups thereof.

Although various exemplary embodiments have been shown and described, the invention is not limited to the embodiments shown. Therefore, the scope of the invention is intended to be limited solely by the scope of the claims that follow.

What is claimed is:

1. An absorptive article comprising a liquid-permeable surface material on a liquid receiving side,
    wherein said surface material is formed of a nonwoven fabric including an upper layer to face the skin of a wearer, and a lower layer positioned under the upper layer,
    wherein at least fibers forming said upper layer contain titanium oxide, and
    wherein the fibers forming said lower layer have a lower elongation percentage and a higher tensile strength than those of the fibers forming said upper layer.

2. An absorptive article according to claim 1,
    wherein the fibers forming said lower layer contain no titanium oxide, or
    wherein the fibers forming said lower layer have a smaller content (in wt. %) of titanium oxide than that (in wt. %) of titanium oxide of the fibers forming said upper layer.

3. An absorptive article according to claim 1,
    wherein the fibers forming said lower layer have an elongation percentage of 50 to 80% and a tensile strength of 2 to 5 g/d.

4. An absorptive article according to claim 2,
    wherein the fibers forming said upper layer contain 0.5 to 10 wt. % of titanium oxide.

5. An absorptive article according to claim 2,
    wherein the fibers forming said lower layer contain 0 to 1 wt. % of titanium oxide.

6. An absorptive article according to claim 1,
    wherein the fibers forming said upper layer are thermoplastic and have a core-sheath structure, the cores of which contain the titanium oxide.

7. An absorptive article according to claim 6,
    wherein the surface material including said upper layer and said lower layer is an air-through bonded nonwoven fabric.

* * * * *